United States Patent [19]
Caron et al.

[11] Patent Number: 6,011,159
[45] Date of Patent: Jan. 4, 2000

[54] PROCESSES AND INTERMEDIATES FOR PREPARING SUBSTITUTED INDAZOLE DERIVATIVES

[75] Inventors: Stephane Caron, Groton; Shane A. Eisenbeis, Pawcatuck, both of Conn.

[73] Assignee: Pfizer Inc, New York, N.Y.

[21] Appl. No.: 09/308,954

[22] PCT Filed: Apr. 28, 1998

[86] PCT No.: PCT/IB98/00647

§ 371 Date: May 27, 1999

§ 102(e) Date: May 27, 1999

[87] PCT Pub. No.: WO98/50367

PCT Pub. Date: Nov. 12, 1998

Related U.S. Application Data

[60] Provisional application No. 60/046,858, May 8, 1997.

[51] Int. Cl.⁷ .................................................. C07D 231/56
[52] U.S. Cl. ............................................................. 548/361.1
[58] Field of Search .......................................... 548/361.1

[56] References Cited

FOREIGN PATENT DOCUMENTS

WO 97/42174  11/1997  WIPO .

*Primary Examiner*—Robert W. Ramsuer
*Attorney, Agent, or Firm*—Peter C. Richardson; Paul H. Ginsburg; Raymond M. Speer

[57] ABSTRACT

The invention relates to processes and intermediates for preparing compounds of formula (I) and pharmaceutically acceptable salts thereof, wherein R, $R^1$, $R^2$, and $R^3$ are as defined herein. The above compounds of formula (I) are selective inhibitors of phosphodiesterase type IV and the production of tumor necrosis factor, and therefore may be used in the treatment of various inflammatory disorders such as asthma, joint inflammation, and other conditions or diseases.

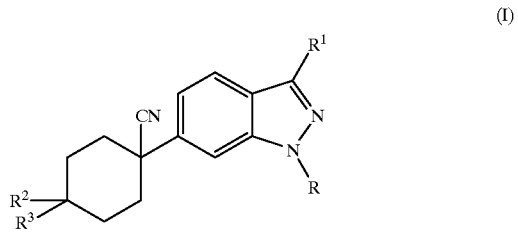

(I)

20 Claims, No Drawings

PROCESSES AND INTERMEDIATES FOR PREPARING SUBSTITUTED INDAZOLE DERIVATIVES

This application claims the benefit of Provisional Application 60/046,858 filed May 8, 1997, and is a 371 of PCT/IB98/00647 filed Apr. 28, 1998.

BACKGROUND OF THE INVENTION

This invention relates to the preparation of substituted indazole derivatives and to intermediates that may be used in said preparation. The substituted indazole derivatives that may be prepared in accord with the present invention are disclosed in U.S. provisional patent application Ser. No. 60/016,861 (filed May 3, 1996), entitled "Substituted Indazole Derivatives And Related Compounds." The foregoing U.S. provisional patent application is incorporated herein by reference in its entirety.

The substituted indazole derivatives that may be prepared in accord with the present invention are selective inhibitors of phosphodiesterase (PDE) type IV and the production of tumor necrosis factor (TNF), as disclosed in U.S. provisional patent application Ser. No. 60/016,861, referred to above. As such, the substituted indazole derivatives that may be prepared in accord with the present invention are useful in the treatment of asthma, joint inflammation, rheumatoid arthritis, gouty arthritis, rheumatoid spondylitis, osteoarthritis and other arthritic conditions, as well as other conditions or diseases involving PDE type IV or the production of TNF.

SUMMARY OF THE INVENTION

The present invention relates to a process for preparing a compound of the formula

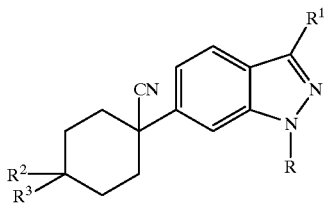

I or a pharmaceutically acceptable salt of said compound, wherein:

R is $C_1$–$C_{10}$ alkyl or —$(CH_2)_n$(phenyl) wherein n is an integer ranging from 0 to 2, and wherein said R groups are optionally substituted by 1 to 3 substituents independently selected from chloro, fluoro, $C_1$–$C_6$ alkoxy and trifluoromethyl;

$R^1$ is $C_1$–$C_{10}$ alkyl, $C_2$–$C_6$ alkenyl or phenyl, wherein said $R^1$ groups are optionally substituted by 1 to 3 substituents independently selected from trifluoromethyl, chloro and fluoro;

$R^2$ is H, —C(Y)$R^4$, —C(O)O$R^4$, —C(Y)N$R^5R^4$, —C(Y)N$R^5$O$R^4$, or —CN;

$R^3$ is H, $C_1$–$C_6$ alkyl optionally substituted by hydroxy, —O$R^4$, —CN, —C(Y)$R^4$, —C(O)O$R^4$, —C(Y)N$R^4R^5$, —C(Y)N$R^4$O$R^5$, —N$R^4$O$R^5$ or —N$R^4R^5$;

or $R^2$ and $R^3$ are taken together to form =O;

each $R^4$ and $R^5$ is independently H or $C_1$–$C_6$ alkyl; and each Y is independently O or S;

which comprises treating a compound of the formula

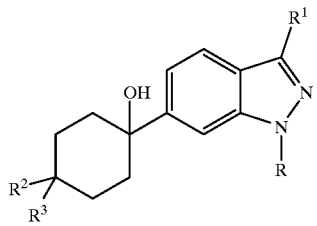

II or a salt of said compound, wherein R, $R^1$, $R^2$ and $R^3$ are as defined above, with a Lewis acid, such as tin tetrachloride, aluminum trichloride, zinc chloride, or boron trichloride, preferably tin tetrachloride, and tri-($C_6$–$C_{10}$ aryl)silyl cyanide, such as triphenylsilyl cyanide, or tri-($C_1$–$C_6$ alkyl) silyl cyanide, preferably trimethylsilyl cyanide.

In the above process of preparing a compound of the formula 1, or a pharmaceutically acceptable salt of said compound, the cyano moiety and $R^3$ in formula I are preferably cis to each other as shown below:

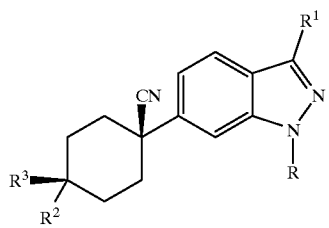

I-a

R is preferably cyclohexyl, cyclopentyl, cyclobutyl, methylene cyclopropyl or isopropyl, $R^1$ is preferably $C_1$–$C_2$ alkyl optionally substituted by 1 to 3 fluoro substituents, $R^2$ is preferably H, and $R^3$ is preferably —C(O)O($C_1$–$C_2$ alkyl), —CH$_2$OH, or —C(O)NH$_2$.

In a further aspect of the present invention, the above compound of the formula II, or a salt of said compound, is prepared by treating a compound of the formula

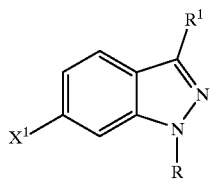

III or a salt of said compound, wherein R and $R^1$ are as defined for the above compound of formula I and $X^1$ is iodo, chloro, or bromo, preferably bromo, with an organolithium, cerium or magnesium reagent, such as $C_1$–$C_{10}$ alkyl lithium, magnesium metal or cerium(III) chloride in combination with an organomagnesium or organolithium reagent, preferably an organolithium reagent such as n-butyllithium, to provide an organometallic intermediate and then treating said organometallic intermediate with a compound of the formula

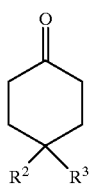

IV wherein $R^2$ and $R^3$ are as defined for the above compound of formula I.

In the above process of preparing the compound of formula II, or a salt of said compound, preferred R, $R^1$, $R^2$ and $R^3$ substituents are as indicated above for the process of preparing a compound of formula I.

In a further aspect of the present invention, the above compound of formula III, or a salt of said compound, is prepared by heating a compound of the formula

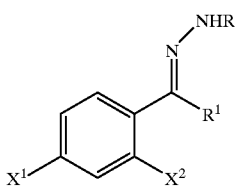

XI or a salt of said compound, wherein $X^1$, R, and $R^1$ are as defined for said compound of formula III, and $X^2$ is iodo, fluoro, bromo, chloro, methanesulfonate, trifluoromethanesulfonate, or phenylsulfonate wherein the phenyl moiety of said phenylsulfonate is optionally substituted by 1 or 2 substituents independently selected from halo, nitro and $C_1$–$C_4$ alkyl, preferably methanesulfonate, to a temperature within the range of about 100° C. to about 200° C.

In the above process of preparing a compound of formula III, or a salt of said compound, preferred R and $R^1$ substituents are as indicated above for the process of preparing a compound of formula I.

In a further aspect of the present invention, the above compound of formula XI, or a salt of said compound, is prepared by treating a compound of the formula

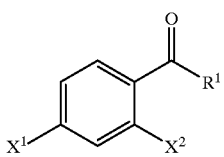

V wherein $X^2$ and $X^1$ are as defined above for said compound of formula XI and $R^1$ is as defined for the above compound of formula I, with a compound of the formula

VI

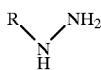

or a salt of said compound, wherein R is as defined for the above compound of formula I, and either an acid, such as ammonium acetate, in which case said compound of formula V is treated with the free base of said compound of formula VI, or a base, such as potassium acetate or sodium acetate, in which case said compound of formula V is treated with a salt of said compound of formula VI.

In the above process of preparing a compound of formula XI, or a salt of said compound, preferred R and $R^1$ substituents are as indicated above for the process of preparing a compound of formula I. Preferred salts of the compound of formula VI are the hydrochloride, hydrobromide, mesylate, tosylate, and oxalate salts of said compound, most preferably the hydrochloride salt of said compound.

In a further aspect of the present invention, the above compound of formula V is prepared by treating a compound of the formula

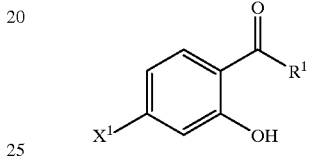

VII wherein $X^1$ is as defined above for said compound of formula III and $R^1$ is as defined for the above compound of formula I, with a base, such as triethylamine, diisopropylethylamine, pyridine optionally substituted by 1 to 3 $C_1$–$C_6$ alkyl groups, potassium hydroxide, or sodium hydroxide, preferably triethylamine, and a second reagent selected from methanesulfonyl chloride, methanesulfonyl anhydride, trifluoromethanesulfonic anhydride, phenylsulfonyl chloride, and phenylsulfonyl anhydride wherein the phenyl moieties of said phenylsulfonyl chloride and phenylsulfonyl anhydride are optionally substituted by 1 or 2 substituents independently selected from halo, nitro and $C_1$–$C_4$ alkyl.

In the above process of preparing the compound of formula V preferred $R^1$ substituents are as indicated above for the process of preparing a compound of formula I and said second reagent is preferably methanesulfonyl chloride.

In a further aspect of the present invention, a compound of the formula

VIII

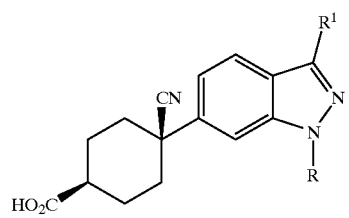

or a pharmaceutically acceptable salt of said compound, wherein R and $R^1$ are as defined for the above compound of formula I, is prepared by treating a compound of the formula

IX

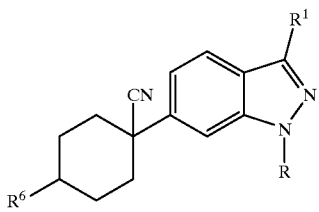

or a salt of said compound, wherein R and $R^1$ are as defined for the above compound of formula I and $R^6$ is —C(O)O ($C_1$–$C_6$ alkyl), CN, —(O)$NR^4R^5$ or —C(O)$NR^4OR^5$ wherein $R^4$ and $R^5$ are as defined for the above compound of formula I, with a base, such as potassium tert-butoxide, sodium ethoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide or sodium methoxide, preferably potassium tert-butoxide, in an alcoholic solvent of the formula $R^7$—OH wherein $R^7$ is $C_1$–$C_6$ alkyl, such as methanol, ethanol, or isopropanol, preferably methanol, to provide a compound of the formula

X

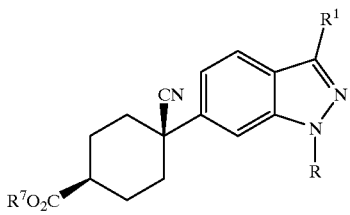

wherein R, $R^1$, and $R^7$ are as defined above, and then hydrolyzing the compound of formula X to provide the compound of formula VIII or a pharmaceutically acceptable salt thereof.

In the above process of preparing a compound of formula VIII, or a pharmaceutically acceptable salt of said compound, preferred R and $R^1$ substituents are as indicated above for the process of preparing the compound of formula I.

The invention also relates to a compound of the formula

V

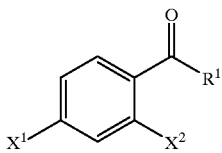

wherein $R^1$ is as defined above for the process of preparing the compound of formula III, $X^1$ is iodo or bromo, preferably bromo, and $X^2$ is methanesulfonate, trifluoromethanesulfonate, or phenylsulfonate wherein the phenyl moiety of said phenylsulfonate is optionally substituted by 1 or 2 substituents independently selected from halo, nitro and $C_1$–$C_4$ alkyl, preferably methanesulfonate. Preferred $R^1$ substituents are as indicated above for the process of preparing a compound of the formula III.

The invention also relates to a compound of the formula

XI

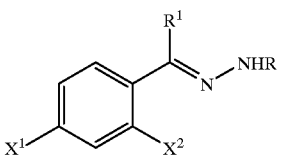

or a salt of said compound, wherein $X^1$, R, and $R^1$ are as defined above for the process of preparing the compound of formula III and $X^2$ is as defined above for the compound of formula V. Preferred substituents are as indicated above for the process of preparing a compound of the formula III and the above compound of formula V.

The term "alkyl", as used herein, unless otherwise indicated, includes saturated monovalent hydrocarbon radicals having straight, cyclic or branched moieties, or combinations thereof. It is understood that for cyclic moieties at least three carbon atoms are required in said alkyl group.

The term "alkoxy", as used herein, unless otherwise indicated, includes —O-alkyl groups wherein "alkyl" is as defined above.

The term "alkenyl", as used herein, unless otherwise indicated, includes alkyl groups, as defined above, which include one or more carbon-carbon double bonds.

The term "aryl", as used herein, unless otherwise indicated, includes an organic radical derived from an aromatic hydrocarbon by removal of one hydrogen, such as phenyl or naphthyl.

The term "halo", as used herein, unless otherwise indicated, includes chloro, fluoro, bromo and iodo.

The phrase "pharmaceutically acceptable salt(s)" or "salt (s)", as used herein, unless otherwise indicated, includes salts of acidic or basic groups which may be present in the compounds of formulas I–XI, referred to above. Where term 'salt(s)" alone is used, it is to be understood that both pharmaceutically acceptable and unacceptable salts are included. The compounds of formulas I–XI that are basic in nature are capable of forming a wide variety of salts with various inorganic and organic acids. The acids that may be used to prepare pharmaceutically acceptable acid addition salts of such basic compounds of formula I–XI are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of formulas I–XI that are acidic in nature are capable of forming base salts with various pharmaceutically acceptable cations. Examples of such salts include the alkali metal or alkaline earth metal salts and, particularly, the calcium, magnesium, amine, sodium and potassium salts of the compounds of formulas I–XI.

Certain compounds of formulas I–XI may have asymmetric centers and therefore exist in different enantiomeric and diastereomic forms. This invention relates to all optical isomers and stereoisomers of the compounds of formulas I–XI, and mixtures thereof, and to the use or preparation of all such isomers and stereoisomers.

The present invention also includes the compounds of formulas I–XI, and the salts or pharmaceutically acceptable salts thereof, wherein one or more hydrogen, carbon or other atom is replaced by an isotope thereof. Such compounds may be useful as research and diagnostic tools in metabolism pharmacokinetic studies and in binding assays.

DETAILED DESCRIPTION OF THE INVENTION

The present invention is illustrated in the following Schemes. Unless otherwise indicated, R, $R^1$, $R^2$, $R^3$, $R^6$, $R^7$, $X^1$ and $X^2$ in the reaction Schemes and discussion that follows are as defined above.

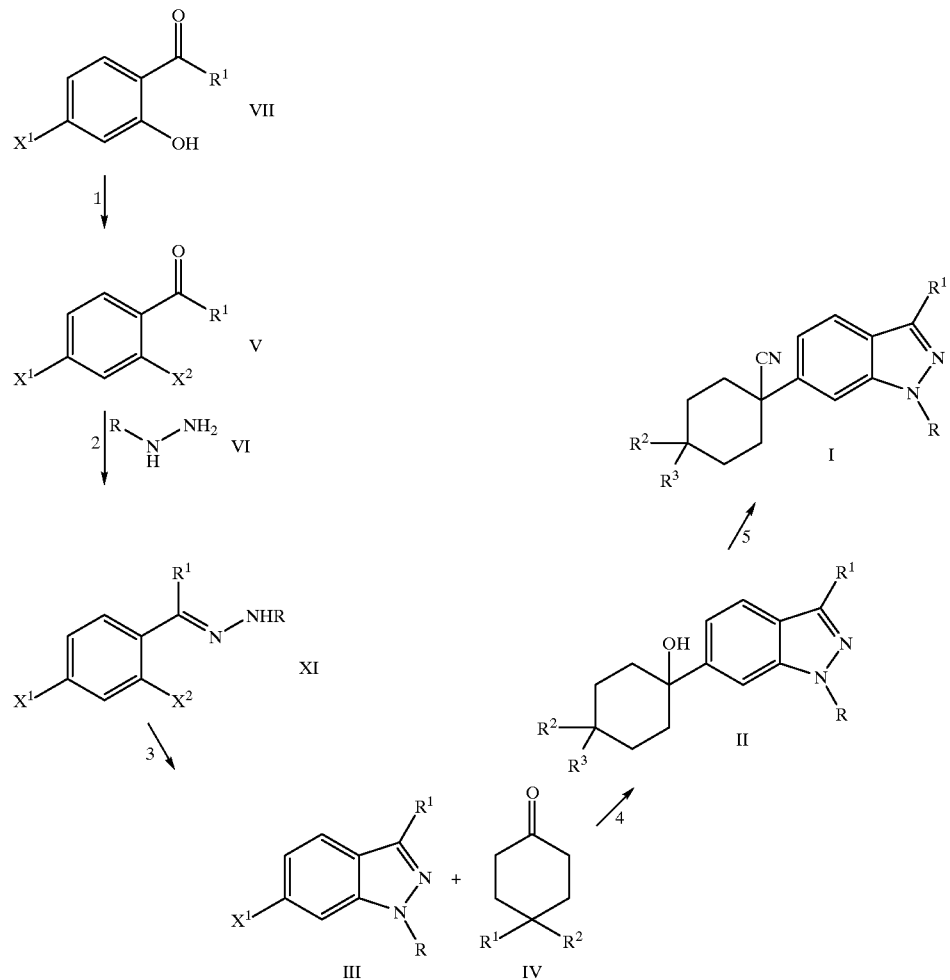

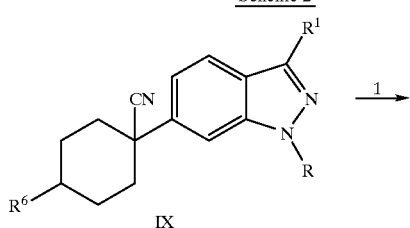

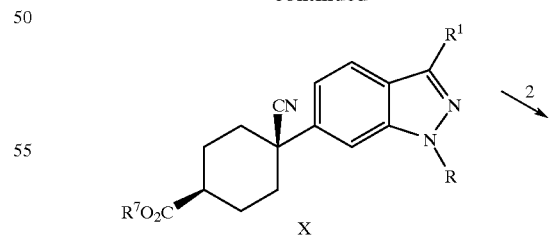

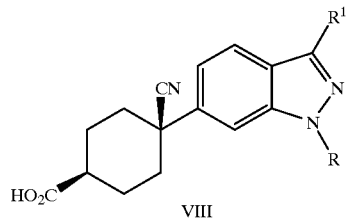

VIII

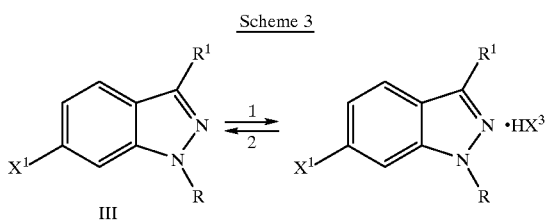

Scheme 3

III

The method of the present invention may be described through reference to Schemes 1–3 above. In Scheme 1, the starting compound of formula VII may be prepared according to methods familiar to those skilled in the art, including one or more synthetic procedures described in R. Martin, J-M Betous, Bulletin de la Société Chimique de France, 1969, pages 2079–2088, and U.S. provisional patent application Ser. No. 60/016,861, referred to above. In step 1 of Scheme 1, the hydroxy group of the compound of formula VII is converted to a leaving group. In this process, the compound of formula VII is treated with a base such as triethylamine, diisopropylethylamine, pyridine optionally substituted by 1 to 3 alkyl groups, potassium or sodium hydroxide, preferably triethylamine, in a solvent such as dichloromethane, dichloroethane, water, or toluene, or a mixture of two or more of the foregoing solvents, preferably dichloromethane, and reacted with an electrophile such as methanesulfonyl chloride or anhydride, phenylsulfonyl chloride or anhydride wherein the phenyl moiety of said phenylsulfonyl optionally includes 1 or 2 substituents selected from halo, nitro and $C_1$–$C_4$ alkyl, or trifluoromethanesulfonic anhydride, preferably methanesulfonyl chloride, at a temperature ranging from about 0° C. to room temperature (20–25° C.) for a period of about ten minutes to about five hours, typically thirty minutes, to provide the compound of formula V.

In step 2 of Scheme 1, the compound of formula V is reacted with a hydrazine derivative of formula VI and an acid, preferably ammonium acetate, in a solvent, preferably a solvent having a high boiling point such as xylenes, toluene, or mesitylene, or a mixture of two or more of the foregoing solvents, preferably xylenes, to provide the compound of formula XI. In general, the compound of formula XI need not be separated or isolated from the reaction mixture. In step 3 of Scheme 1, the reaction mixture containing the compound of formula XI is heated at a temperature between about 100° C. and about 200° C., preferably between about 100° C. and about 140° C., for a period of about ten hours to about five days, preferably two days, to provide the compound of formula III. Alternatively, the process of step 2 of Scheme 1 may be accomplished using a salt of the hydrazine derivative of formula VI, such as the hydrochloride, hydrobromide, mesylate, tosylate, or oxalate salt of said compound, preferably the hydrochloride salt, which is reacted with a base, such as sodium or potassium acetate, in a solvent, preferably a solvent having a high boiling point such as xylenes, toluene, or mesitylene, or a mixture of two or more of the foregoing solvents, preferably xylenes.

In step 4 of Scheme 1, the compound of formula III is converted to an organometallic intermediate such as the lithium, cerium or magnesium intermediate of said compound of formula III, which may be formed by treating the compound of formula III with an organolithium, magnesium, or cerium reagent, such as $C_1$–$C_{10}$ alkyl lithium, magnesium metal or cerium(III) chloride in combination with an organomagnesium or organolithium reagent, preferably an organolithium reagent such as n-butyllithium, in a solvent such as tetrahydrofuran, diethyl ether, methyl tert-butyl ether, diisopropyl ether, or toluene, or a mixture of two or more of the foregoing solvents, preferably toluene containing tetrahydrofuran, at a temperature between about –100° C. to about 0° C., preferably –78° C., for a period of about 10 minutes to about 1 hour, preferably 30 minutes. The organometallic intermediate is then reacted with a compound of formula IV in a solvent such as tetrahydrofuran, diethyl ether, methyl tert-butyl ether, diisopropyl ether, or toluene, or a mixture of two or more of the foregoing solvents, preferably toluene, at a temperature ranging from about –100° C. to about 0° C., preferably –78° C., for a period of about 10 minutes to about 2 hours, preferably 45 minutes, to provide the compound of formula II.

Step 5 of Scheme 1 represents the conversion of a tertiary alcohol to a nitrile. In this process, the compound of formula II is treated with a Lewis acid, such as tin tetrachloride, aluminum trichloride, zinc chloride, or boron trichloride, preferably tin tetrachloride, and tri-($C_6$–$C_{10}$ aryl)silyl cyanide, such as triphenylsilyl cyanide, or tri-($C_1$–$C_6$ alkyl) silyl cyanide, preferably trimethylsilyl, in a solvent such as dichloromethane, dichloroethane, or toluene, or a mixture of two or more of the foregoing solvents, preferably dichloromethane, at a temperature ranging from about 0° C. to room temperature (20–25° C.) for a period of about 1 to 48 hours, preferably 24 hours, to provide the compound of formula I.

Scheme 2 illustrates the epimerization of a stereocenter followed by hydrolysis of an ester to an acid. The compound of formula IX, wherein $R^6$ is an epimerizable moiety as defined above, is treated with a base such as potassium tert-butoxide, sodium ethoxide, sodium hydride, 1,1,3,3-tetramethylguanidine, 1,8-diazabicyclo[5.4.0]undec-7ene, 1,5-diazabicylo-[4.3.0]non-5ene, potassium ethoxide, or sodium methoxide, preferably potassium tert-butoxide, in an alcoholic solvent of the formula $R^7$—OH, wherein $R^7$ is $C_1$–$C_6$ alkyl, such as methanol, ethanol, or isopropanol, preferably methanol, to provide the compound of formula X. In this step, a mixture of cis and trans diastereomers will generally form, but the cis diastereomer (the compound of formula X) may predominate over the trans diastereomer as the thermodynamically favored species. Water or sodium hydroxide is then added to the reaction mixture which is stirred for a period of about 1 to 48 hours, preferably 12 hours, to hydrolyze the $R^7$ ester moiety to a carboxylic acid and thus provide the compound of formula VIII. In this step, the sodium or potassium base salt of the acid moiety may form with the compound of formula VIII. This salt may be converted to the carboxy moiety as shown for the compound of formula VIII through the addition of an acid such as hydrochloric acid.

Scheme 3 illustrates a procedure to facilitate the handling and purification of the indazole intermediate of formula III which is described above in reference to Scheme 1. In step 1 of Scheme 3, the indazole of formula III is treated with an acid, such as hydrobromic, hydrochloric, or sulfuric acid, preferably hydrobromic acid, in a solvent such as toluene, xylenes, acetic acid, or ethyl acetate, preferably toluene, at a temperature ranging from 0° C. to ambient temperature (20–25° C.), preferably ambient temperature, to form a salt of the compound of formula III, wherein $HX^3$ indicates the acid used to prepare the salt and $X^3$ is the anion of said acid. The salt may be separated and purified according to methods familiar to those skilled in the art. In step 2 of Scheme 3, the salt is converted back to the free base. In this step, the salt of the compound of formula III is treated with an aqueous base, such as sodium hydroxide, potassium hydroxide, sodium carbonate, sodium bicarbonate, potassium carbonate, or potassium bicarbonate, preferably sodium hydroxide, in a solvent such as hexanes, toluene, dichloromethane, diisopropyl ether, methyl tert-butyl ether, or ethyl acetate, preferably toluene, at a temperature ranging from 0° C. to ambient temperature (20–25° C.), preferably ambient temperature, for a period of 5 minutes to 1 hour, preferably 10 minutes, to provide the compound of formula III.

The compounds of the formulas I–X may have asymmetric carbon atoms and therefore exist in different enantiomeric and diastereomeric forms. Diastereomeric mixtures can be separated into their individual diastereomers on the basis of their physical chemical differences by methods known to those skilled in the art for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. The use of all such isomers, including diastereomer mixtures and pure enantiomers, are considered to be part of the present invention.

The compounds of formulas I–X that are basic in nature are capable of forming a wide variety of different salts with various inorganic and organic acids. Although such salts must be pharmaceutically acceptable for administration to mammals, it is often desirable in practice to initially isolate the compound of formula I–X from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of formula I–X that are acidic in nature are capable of forming base salts with various cations. For compounds that are to be administered to mammals, such salts must be pharmaceutically acceptable. Where a pharmaceutically acceptable salt is required, it may be desirable to initially isolate the compound of formula I–X from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of formulas I–X. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantifies of reagents are preferably employed in order to ensure completeness of reaction and maximum yields of the desired final product The following Examples further illustrate the method and intermediates of the present invention. It is to be understood that the present invention is not limited to the specific details of the Examples provided below.

EXAMPLE 1

Methanesulfonic acid 5-bromo-2-propionyl-phenyl ester

To a solution of 1-(4-bromo-2-hydroxy-phenyl)-propan-1-one (20.0 g, 87.3 mmol) in dichloromethane (100 mL) was added triethylamine (24.3 mL, 174 mmol). The resulting solution was cooled to 0° C. and methanesulfonyl chloride (8.10 mL, 105 mmol) was added dropwise. The reaction was stirred for 30 minutes, poured into 1N aqueous hydrochloric acid (100 mL) and the layers were separated. The aqueous layer was extracted with dichloromethane (50 mL), the organic layers were combined, dried over magnesium sulfate, filtered, and concentrated to an oil which crystallized upon standing. The solid was recrystallized from a 60/40 mixture of ethanol and water (40 mL) to provide methanesulfonic acid 5-bromo-2-propionyl-phenyl ester (21.8 g, 81% yield). $^1$H NMR (400 MHz, $CDCl_3$) δ 1.17 (t, 3, J=7.3), 2.90 (q, 2, J=7.3), 3.24 (s, 3), 7.51–7.56 (m, 2), 7.59 (d, 1, J=1.3). $^{13}$C NMR (100 MHz, $CDCl_3$) δ 8.04, 35.45, 38.51, 128.18, 127.08, 130.60, 130.69, 131.82, 146.15, 200.30. IR 3049, 2940, 1691, 1590, 1343, 959, 886 $cm^{-1}$. Analysis calculated for $C_{10}H_{12}BrO_4S$: C, 39.10; H, 3.61. Found: C, 38.90; H, 3.70.

EXAMPLE 2

6-Bromo-1-cyclohexyl-3-ethyl-1H-indazole

Methanesulfonic acid 5bromo-2-propionyl-phenyl ester (36.6 g, 119 mmol) was combined with cyclohexylhydrazine (27.2 g, 238 mmol) and ammonium acetate (23.0 g, 299 mmol) in xylenes (220 mL). The reaction mixture was heated to 135° C. in a Dean-Stark apparatus for 48 hours. The reaction was cooled to room temperature and concentrated to a low volume under reduced pressure. The crude product was filtered through a pad of silica gel (weight ratio product/silica gel 1/5) eluting first with hexanes then with a 10/90 mixture of ethyl acetate and hexanes. The fractions containing principally 6-bromo-1-cyclohexyl-3-ethyl-1H-indazole were collected. A second crop was obtained by repeating the above silica treatment with the mixed fractions. The two crops were combined and dried under vacuum to yield 28.0 g of 6-bromo-1-cyclohexyl-3-ethyl-1H-indazole (76% yield). $^1$H NMR (400 MHz, CDCl$_3$) δ 1.35 (t, 3, J=7.7), 1.39–2.06 (m, 10), 2.95 (q, 2, J=7.7), 4.21–4.28(m, 1), 7.15 (d, 1, J=8.5), 7.51 (d, 1, J=8.5), 7.56 (s, 1). $^{13}$C NMR (100 MHz, CDCl$_3$) δ 13.95, 20.50, 25.35, 25.84, 32.44, 58.15, 112.01, 120.10, 121.37, 121.65, 122.82, 140.37, 146.60. IR 2934, 2855, 1606, 1502, 1451, 1048, 951, 834 cm$^{-1}$. Analysis calculated for C$_{15}$H$_{19}$BrN$_2$: C, 58.64; H, 6.23; N, 9.12. Found: C, 58.82; H, 6.20; N, 9.01.

EXAMPLE 3

6-Bromo-1-methyl-3-ethyl-1H-indazole

Methanesulfonic acid 5-bromo-2-propionyl-phenyl ester (2.00 g, 6.51 mmol) was combined with methylhydrazine (0.69 mL, 13 mmol) and ammonium acetate (1.30 g, 16.9 mmol) in xylenes (12 mL). The reaction mixture was heated to 135° C. for 18 hours using a Dean Stark apparatus. The reaction was cooled to room temperature, diluted with dichloromethane (50 mL), and washed with water (50 mL) and 1N aqueous hydrochloric acid (50 mL). The organic extracts were dried over magnesium sulfate and concentrated. The crude product was purified by chromatography on silica gel eluting with 4:1 hexanes/ethyl acetate to yield 1.20 g of 6-bromo-1-methyl-3ethyl-1H-indazole (75% yield). $^1$H NMR (400 MHz, CDCl$_3$) δ 1.35 (t, 3, J=7.7), 2.94 (q, 2, J=7.7), 3.95 (s, 3), 7.18 (dd, 1, J=8.5, 1.5), 7.50 (d, J=0.8), 7.52 (dd, 1, J=8.5, 0.6). $^{13}$C NMR (100 MHz, CDCl$_3$) δ 13.66, 20.29, 35.21, 111.82, 120.61, 121.35, 121.60, 123.05, 141.68, 147.08. IR 2970, 2935, 1609, 1506, 1458, 1223, 1047, 819, 805 cm$^{-1}$. Analysis calculated for C$_{10}$H$_{11}$BrN$_2$: C, 50.23; H, 4.64; N, 11.72. Found: C, 50.14; H, 4.57; N, 11.46.

EXAMPLE 4

6-Bromo-1-benzyl-3-ethyl-1H-indazole

Methanesulfonic acid 5-bromo-2-propionyl-phenyl ester (5.00 g, 16.3 mmol) was combined with benzylhydrazine dihydrochloride (4.45 g, 22.8 mmol) and sodium acetate (4.01 g, 48.9 mmol) in xylenes (30 mL). The reaction mixture was heated to 135° C. for two days using a Dean Stark apparatus. The reaction was cooled to room temperature, diluted with dichloromethane (75 mL), and washed with water (75 mL) and 1N aqueous hydrochloric acid (75 mL). The organic extracts were dried over magnesium sulfate and concentrated. The crude product was purified by chromatography on silica gel eluting with 4:1 hexanes/ethyl acetate to yield 2.10 g of 6-bromo-1-benzyl-3ethyl-1H-indazole (41% yield). $^1$H NMR (400 MHz, CDCl$_3$) δ 1.39 (t, 3, J=7.7), 2.96 (q, 2, J=7.7), 5.48 (s, 2), 7.14–7.23 (m, 3), 7.26–7.31 (m, 3), 7.42 (s, 1), 7.54 (d, 1, J=8.5). $^{13}$C NMR (100 MHz, CDCl$_3$) δ 13.70, 20.37, 52.68, 112.12, 120.77, 121.69, 121.83, 123.34, 126.97, 127.76, 128.75, 136.74, 141.37, 147.60. IR 3064, 3031, 2970, 2934, 2875, 1606, 1504, 1497, 1454, 1236, 1048, 831, 701 cm$^1$. Analysis calculated for C$_{16}$H$_{15}$BrN$_2$: C, 60.97; H, 4.80; N, 8.89. Found: C, 61.21; H, 4.92; N, 8.73.

EXAMPLE 5

6-Bromo-3-ethyl-1-(4-methoxy-phenyl)-1H-indazole

Methanesulfonic acid 5-bromo-2-propionyl-phenyl ester (5.00 g, 16.3 mmol) was combined with 4-methoxyphenylhydrazine hydrochloride (4.00 g, 22.9 mmol) and sodium acetate (4.01 g, 48.9 mmol) in xylenes (30 mL). The reaction mixture was heated to 135° C. for 36 hours using a Dean Stark apparatus. The reaction was cooled to room temperature, diluted with dichloromethane (50 mL), and washed with water (50 mL) and 1N aqueous hydrochloric acid (50 mL). The organic extract were dried over magnesium sulfate and concentrated. The crude product was purified by chromatography on silica gel eluting with 4:1 hexanes/ethyl acetate to yield 2.14 g of 6-bromo-3-ethyl-1-(4-methoxy-phenyl)-1H-indazole (40% yield). $^1$H NMR (400 MHz, CDCl$_3$) δ 1.43 (t, 3, J=7.7), 3.00 (q, 2, J=7.7), 3.86 (s, 3), 7.03 (d, 2, J=8.9), 7.25 (dd, 1, J=8.5, 1.5), 7.53 (d, 2, J=9.1), 7.58 (d, 1, J=8.5), 7.73 (d, 1, J=1.5). $^{13}$C NMR (100 MHz, CDCl$_3$) δ 13.53, 20.34, 55.61, 113.02, 114.70, 121.33, 121.70, 122.45, 123.93, 124.50, 132.90, 140.67, 148.83, 158.42. IR 2970, 2934, 1604, 1519, 1461, 1442, 1300, 1250, 1050, 1035, 945, 832 cm$^{-1}$. Analysis calculated for C$_{16}$H$_{15}$BrN$_2$O: C, 58.02; H, 4.56; N, 8.46. Found: C, 58.39; H, 4.69; N, 8.13.

EXAMPLE 6

4-(1-Cyclohexyl-3-ethyl-1H-indazol-6-yl)-4-hydroxy-cyclohexanecarboxylic acid ethyl ester To a solution of 6bromo-1-cyclohexyl-3-ethyl-1H-indazole (12.7 g, 41.3 mmol) in toluene (64 mL) was added tetrahydrofuran (6.70 mL, 82.6 mmol). The solution was cooled to −78° C. and n-butyllithium (17.3 mL of a 2.5M solution in hexanes, 43.4 mmol) was added dropwise. The solution was stirred 10 minutes and added to a solution of 4-oxo-cyclohexanecarboxylic acid ethyl ester (8.80 g, 51.7 mmol) in toluene (127 mL) at −78° C. The reaction mixture was stirred for 15 minutes and poured into 1N aqueous hydrochloric acid (200 mL). The layers were separated and the aqueous layer was reextracted with toluene (60 mL). The organic extracts were combined and dried over magnesium sulfate, filtered, and concentrated to an oil which was purified by filtration through a pad of silica gel eluting with 4:1 hexanes/ethyl acetate. The product-rich fractions were concentrated to yield 4-(1-cyclohexyl-3-ethyl-1H-indazol-6-yl)-4-hydroxy-cyclohexanecarboxylic acid ethyl ester (13.5 g, 82%) as a mixture of diastereoisomers. Upon standing, one of the diastereoisomers crystallized and was isolated by trituration with hexanes. $^1$H NMR (400 MHz, CDCl$_3$) δ 1.25–1.40 (m, 4), 1.27 (t, 3, J=7.1), 1.35 (t, 3, J=7.7), 1.65–2.07 (m, 15), 2.37–2.44 (m, 1), 2.96 (q, 2, J=7.7), 4.15 (q, 2, J=7.1), 4.30–4.38 (m, 1), 7.13 (d, 1, J=8.5), 7.58 (s, 1), 7.63 (d, 1, J=8.5). $^{13}$C NMR (100 MHz, CDCl$_3$) δ 14.16, 14.26, 20.69, 24.60, 25.39, 25.91, 32.54, 38.22, 42.57, 57.59, 60.34, 72.80, 104.49, 116.80, 120.28, 121.26, 139.84, 146.09, 146.93, 175.63. Analysis calculated for C$_{24}$H$_{34}$N$_2$O$_3$: C, 72.33; H, 8.60; N, 7.03. Found: C, 72.11; H, 8.55; N, 6.92.

EXAMPLE 7

4-Cyano-4(1-cyclohexyl-3-ethyl-1H-indazol-6-yl)-cyclohexanecarboxylic acid ethyl ester To solution of 4-(1-cyclohexyl-3-ethyl-1H-indazol-6-yl)-4-hydroxy-cyclohexanecarboxylic acid ethyl ester (13.5 g, 33.9 mmol) in dichloromethane (135 mL) cooled to 0° C. was added trimethylsilyl cyanide (22.6 mL, 169 mmol) followed by a slow addition of tin tetrachloride (13.6 mL of a 1.0 M solution in dichloromethane, 13.6 mmol). The reaction mixture was allowed to warm to room temperature overnight. Potassium carbonate (18.7 g, 136 mmol) and potassium fluoride dihydrate (12.8 g, 136 mmol) were added, followed by dropwise addition of water (4.30 mL, 239 mmol). The reaction mixture was stirred vigorously for 90 minutes after which silica gel (25 g) was added. The mixture was filtered and washed thoroughly with dichloromethane. The filtrate was washed with saturated aqueous NaHCO$_3$ (250 mL), dried over magnesium sulfate, filtered and concentrated to an oil to yield 13.2 g (96% yield) of 4-cyano-(1-cyclohexyl-3-ethyl-1H-indazol-6yl)-cyclohexanecarboxylic acid ethyl ester as a mixture of diastereoisomers. For characterization purposes, a sample of each diastereoisomer was obtained by purification by chromatography on silica gel eluting with 4:1 hexanes/ethyl acetate. Higher Rf diastereoisomer $^1$H NMR (400 MHz, CDCl$_3$) δ 1.28 (t, 3, J=7.1), 1.36 (t, 3, J=7.7), 1.43–1.56 (m, 2), 1.74–1.77 (m, 2), 1.93–2.10 (m, 10), 2.20–2.24 (m, 2), 2.31 (d, 2, J =12.9), 2.30 (tt, 1, J=12.2, 3.5), 2.95 (q, 2, J=7.7), 4.15 (q, 2, J=7.1), 4.29–4.37 (m, 1), 7.13 (d, 1, J=8.5), 7.52 (s, 1), 7.68 (d, 1, J=8.5). $^{13}$C NMR (100 MHz, CDCl$_3$) δ 14.06, 14.23, 20.62, 25.35, 25.81, 26.20, 32.57, 36.77, 42.15, 44.27, 57.67, 60.63, 106.08, 116.96, 121.22, 121.95, 122.19, 138.23, 139.61, 146.31, 174.30. Analysis calculated for C$_{25}$H$_{33}$BrN$_3$O$_2$: C, 73.68; H, 8.15; N, 10.31. Found: C, 73.58; H, 8.28; N, 10.38. Lower Rf diastereoisomer: mp 89–91° C. $^1$H NMR (400 MHz, CDCl$_3$) δ 1.26 (t, 3, J=7.1), 1.33 (t, 3, J=7.7), 1.40–1.54 (m, 2), 1.71–1.78 (m, 2), 1.89–2.19 (m, 13), 2.23–2.31 (m, 2), 2.94 (q, 2, J=7.7), 4.17(q, 2, J=7.1), 4.26–4.33 (m, 1), 7.10 (d, 1, J=8.5), 7.47 (s, 1), 7.64 (d, 1, J=8.5). $^{13}$C NMR (100 MHz, CDCl$_3$) δ 14.07, 14.29, 24.71, 25.35, 25.80, 32.58, 33.74, 37.57, 44.26, 57.59, 60.59, 106.05, 117.26, 121.16, 121.85, 122.61, 138.42, 139.60, 146.27, 174.47. Analysis calculated for C$_{25}$H$_{33}$BrN$_3$O$_2$: C, 73.68; H, 8.15; N, 10.31. Found: C, 73.62; H. 8.53; N, 10.30.

EXAMPLE 8

Cis4-cyano-4-(1-cyclohexyl-3-ethyl-1H-indazol-6-yl)-cyclohexanecarboxylic acid

To a solution of 4-Cyano-4(1-cyclohexyl-3-ethyl-1H-indazol-6-yl)-cyclohexanecarboxylic acid ethyl ester (13.0 g, 31.9 mmol) as a mixture of cis and trans diastereoisomers in ethanol (130 mL) was added potassium tert-butoxide in portions (10.7 g, 95.3 mmol). The solution was stirred at room temperature for 7 hours and then water (2.00 mL, 111 mmol) was added. The reaction mixture was stirred until consumption of the starting material (14 hours). The solvent was evaporated under reduced pressure and the crude product was dissolved in dichloromethane (100 mL) and washed with 1N aqueous hydrochloric acid (100 mL). The layers were separated and the organic extract was dried over magnesium sulfate, filtered, and concentrated. The crude product was dissolved in toluene (50 mL) and p-toluenesulfonic acid (100 mg) was added. The solution was stirred at 100° C. for 4 hours, cooled to room temperature, and concentrated. The crude product was dissolved in hot ethyl acetate (35 mL) and hexanes (35 mL) was added. The solution was allowed to cool to 0° C. and stirred 12 hours. The solids were filtered, and washed with hexanes to provide 3.50 g of cis-4cyano-4-(1-cyclohexyl-3ethyl-1H-indazol-6-yl)-cyclohexanecarboxylic acid (29% yield). $^1$H NMR (400 MHz, CDCl$_3$) δ 1.34 (t, 3, J=7.9), 1.42–1.51 (m, 2), 1.74 (d, 1, J=12.9), 1.90–2.13 (m, 11), 2.23–2.33 (m, 4), 2.46 (tt, 1, J=12.0, 3.5), 2.96 (q, 2, J=7.9), 4.28–4.36 (m, 1), 7.13 (dd, 1, J =8.5, 1.3), 7.67 (d, 1, J=8.3). $^{13}$C NMR (100 MHz, CDCl$_3$) δ 13.97, 20.47, 25.27, 25.76, 25.91, 32.47, 36.57, 41.64, 44.14, 57.70, 106.05, 116.96, 121.25, 121.88, 122.01, 138.15, 139.53, 146.34, 179.80.

EXAMPLE 9

6-Bromo-1-cyclohexyl-3-ethyl-1H-indazole hydrobromide

6-Bromo-1-cyclohexyl-3-ethyl-1H-indazole (1.015 g, 3.304 mmol) was dissolved in toluene (10 mL) and to the solution was added hydrobromic acid (1.5 mL of a 30% solution in acetic acid). The solution was stirred at room temperature 30 minutes and concentrated to low volume. Ethyl acetate (10 mL) was added, the solids were filtered and washed with additional ethyl acetate (10 mL) to provide 6-bromo-1 cyclohexyl-3-ethyl-1H-indazole hydrobromide (1.612 g, 80%) as a white solid (mp 170–172° C. (decomposition)). $^1$H NMR (400 MHz, DMSO) δ 1.24 (t, 3, J=7.5), 1.42–1.45 (m, 2), 1.64 (d, 1, J=12.9), 1.76–1.87 (m, 7), 2.85 (q, 2, J=7.5), 4.46–4.52 (m, 1), 7.14 (dd, 1, J=8.5, 1.5), 7.63 (dd, 1, J=8.5, 0.8), 7.93 (d, 1, J=1.0), 9.93 (bs, 1). $^{13}$C NMR (100 MHz, DMSO) δ 13.99, 20.23, 25.47, 32.70, 56.67, 112.69, 119.90, 121.06, 122.42, 122.98, 140.57, 146.18.

EXAMPLE 10

6-Bromo-1-cyclohexyl-3-ethyl-1H-indazole

To 6-bromo-1-cyclohexyl-3-ethyl-1H-indazole hydrobromide (0.890 g, 2.30 mmol) was added 1N aqueous sodium hydroxide (20 mL) and toluene (20 mL). The biphasic mixture was stirred for one hour and the layers separated. The aqueous layer was reextracted with toluene (10 mL), and the organic extracts were combined, dried over magnesium sulfate, and concentrated to provide 6-bromo-1-cyclohexyl-3ethyl-1H-indazole (0.660 g, 94% yield). $^1$H NMR (400 MHz, CDCl$_3$) δ 1.35 (t, 3, J=7.7), 1.39–2.06 (m, 10), 2.95 (q, 2, J=7.7), 4.21–4.28 (m, 1), 7.15 (d, 1, J=8.5), 7.51 (d, 1, J=8.5), 7.56 (s, 1). $^{13}$C NMR (100 MHz, CDCl$_3$) δ 13.95, 20.50, 25.35, 25.84, 32.44, 58.15, 112.01, 120.10, 121.37, 121.65, 122.82, 140.37, 146.60. IR 2934, 2855, 1606, 1502, 1451, 1048, 951, 834 cm$^1$. Analysis calculated for C$_{15}$H$_{19}$BrN$_2$: C, 58.64; H, 6.23; N, 9.12. Found: C, 58.82; H, 6.20; N, 9.01.

EXAMPLE 11

Cis-4-cyano-4(1-cyclohexyl-3-ethyl-1H-indazol-6-yl)-cyclohexanecarboxylic acid methyl ester To solution of 4-cyano-4-(1-cyclohexyl-3-ethyl-1H-indazol-6-yl)-cyclohexanecarboxylic acid ethyl ester (1.34 g, 3.29 mmol) in methanol (5.0 mL) was added methyl acetate (0.2 mL) and potassium tert-butoxide (0.506 g, 4.51 mmol). The reaction was stirred 16 hours at room temperature and the solids were filtered and washed with methanol to provide cis-4-cyano-4-(1-cyclohexyl-3ethyl-1H-indazol-6-yl)-cyclohexanecarboxylic acid methyl ester (0.690 g, 53% yield) as a white solid. mp 158–159° C. $^1$H NMR (400 MHz, CDCl$_3$) δ 1.36 (t, 3, J=7.7), 1.42–1.54 (m, 2), 1.74–1.78 (m, 1), 1.92–2.20 (m, 11), 2.22 (dd, 2, J=13.9, 2.7), 2.31 (d, 2, J=12.5), 2.42 (tt, 1, J=12.1, 3.5), 2.98 (q, 2, J=7.7), 3.72 (s, 3), 4.30–4.37 (m, 1), 7.13 (d, 1, J=8.5), 7.52 (s, 1), 7.68 (d, 1, J=8.5). $^{13}$C NMR (100 MHz, CDCl$_3$) δ 14.06, 20.62, 25.35, 25.82, 26.20, 32.58, 36.73, 42.02, 44.25, 51.89, 57.67, 106.08, 116.97, 121.23, 121.96, 122.18, 138.19, 139.61, 146.31, 174.73.

What is claimed is:

1. A process for preparing a compound of the formula

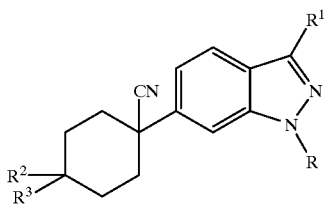

I or a pharmaceutically salt of said compound, wherein:

R is $C_1$–$C_{10}$ alkyl or —$(CH_2)_n$(phenyl) wherein n is an integer ranging from 0 to 2, and wherein said R groups are optionally substituted by 1 to 3 substituents independently selected from chloro, fluoro, $C_1$–$C_6$ alkoxy and trifluoromethyl;

$R^1$ is $C_1$–$C_{10}$ alkyl, $C_2$–$C_6$ alkenyl or phenyl, wherein said $R^1$ groups are optionally substituted by 1 to 3 substituents independently selected from trifluoromethyl, chloro and fluoro;

$R^2$ is H, —$C(Y)R^4$, —$C(O)OR^4$, —$C(Y)NR^5R^4$, —$C(Y)NR^5OR^4$, or —CN;

$R^3$ is H, $C_1$–$C_6$ alkyl optionally substituted by hydroxy, -$OR^4$, —CN, —$C(Y)R^4$, —$C(O)OR^4$, —$C(Y)NR^4R^5$, —$C(Y)NR^4OR^5$, —$NR^4OR^5$ or —$NR^4R^5$;

or $R^2$ and $R^3$ are taken together to form =O;

each $R^4$ and $R^5$ is independently H or $C_1$–$C_6$ alkyl; and, each Y is O or S;

which comprises treating a compound of the formula

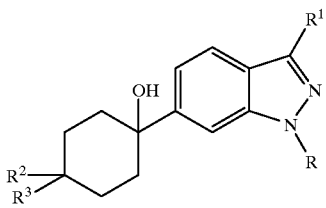

II or a salt of said compound, wherein R, $R^1$, $R^2$ and $R^3$ are as defined for said compound of formula I, with a Lewis acid and tri-($C_6$–$C_{10}$ aryl)silyl cyanide or tri-($C_1$–$C_6$ alkyl)silyl cyanide.

2. The process of claim 1 wherein the cyano moiety and $R^3$ in formula I are cis to each other as follows:

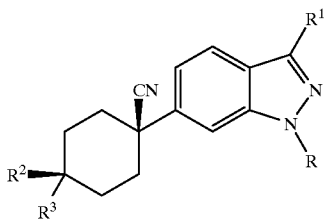

I-a and said Lewis acid is selected from tin tetrachloride, aluminum trichloride, zinc chloride, and boron trichloride, said compound of formula II, or a salt thereof, is treated with trimethylsilyl cyanide, R is selected from cyclohexyl, cyclobutyl, cyclopentyl, methylene cyclopropyl and isopropyl, $R^1$ is $C_1$–$C_2$ alkyl optionally substituted by 1 to 3 fluoro substituents, $R^2$ is H, and $R^3$ is —$C(O)O(C_1$–$C_2$ alkyl), —$CH_2OH$, or —$C(O)NH_2$.

3. The process of claim 2 wherein said Lewis acid is tin tetrachloride, R is cyclohexyl, $R^1$ is ethyl, and $R^3$ is —$C(O)O(C_1$–$C_2$ alkyl).

4. The process of claim 1 wherein the compound of the formula II, or a salt of said compound, is prepared by treating a compound of the formula

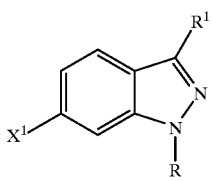

III or a salt of said compound, wherein $X^1$ is iodo, chloro or bromo, R and $R^1$ are as defined in claim 1, with a magnesium, cerium or organolithium reagent and then treating the resulting organometallic intermediate with a compound of the formula

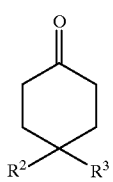

IV wherein $R^2$ and $R^3$ are as defined in claim 1.

5. The process of claim 4 wherein said compound of formula III is treated with an organolithium reagent which is $C_1$–$C_{10}$ alkyl lithium, $X^1$ is bromo, R is selected from cyclohexyl, cyclobutyl, cyclopentyl, methylene cyclopropyl and isopropyl, $R^1$ is $C_1$–$C_2$ alkyl optionally substituted by 1 to 3 fluoro substituents, $R^2$ is H, and $R^3$ is —$C(O)O(C_1$–$C_2$ alkyl), —$CH_2OH$, or —$C(O)NH_2$.

6. The process of claim 5 wherein said organolithium reagent is n-butyllithium, R is cyclohexyl, $R^1$ is ethyl, and $R^3$ is —$C(O)O(C_1$–$C_2$ alkyl).

7. The process of claim 4 wherein the compound of formula III, or a salt of said is compound, is prepared by heating a compound of the formula

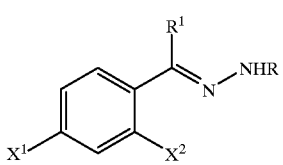

XI or a salt of said compound, wherein $X^1$, R and $R^1$ are as defined in claim 4, and $X^2$ is iodo, fluoro, bromo, chloro, methanesulfonate, trifluoromethanesulfonate, or phenylsulfonate wherein the phenyl moiety of said phenylsulfonate is optionally substituted by 1 or 2 substituents independently selected from halo, nitro and $C_1$–$C_4$ alkyl, to a temperature within the range of about 100° C. to about 200° C.

8. The process of claim 7 wherein $X^2$ is methanesulfonate, $X^1$ is bromo, R is selected from cyclohexyl, cyclopentyl, methylene cyclopropyl and isopropyl, $R^1$ is $C_1$–$C_2$ alkyl optionally substituted by 1 to 3 fluoro substituents and said compound of formula XI, or a salt of said compound, is heated to a temperature within the range of about 100° C. to about 140° C.

9. The process of claim 8 wherein R is cyclohexyl and $R^1$ is ethyl.

10. The process of claim 7 wherein the compound of formula XI, or a salt of said compound, is prepared by treating a compound of the formula

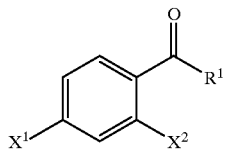

V wherein $X^1$, $X^2$ and $R^1$ are as defined in claim 7, with a compound of the formula

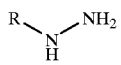

VI or a salt of said compound, wherein R is as defined in claim 7, and either an acid, where said compound of formula V is treated with the free base of said compound of formula VI, or a base, where said compound of formula V is treated with a salt of said compound of formula VI.

11. The process of claim 10 wherein said compound of formula V is treated with the hydrochloride, hydrobromide, mesylate, tosylate, or oxalate salt of said compound of formula VI, $X^2$ is methanesulfonate, said base is potassium acetate or sodium acetate, $X^1$ is bromo, R is selected from cyclohexyl, cyclopentyl, methylene cyclopropyl and isopropyl, and $R^1$ is $C_1$–$C_2$ alkyl optionally substituted by 1 to 3 fluoro substituents.

12. The process of claim 10 wherein said compound of formula V is treated with the free base of said compound of formula VI, $X^2$ is methanesulfonate, said acid is ammonium acetate, $X^1$ is bromo, R is selected from cyclohexyl, cyclobutyl, cyclopentyl, methylene cyclopropyl and isopropyl, and $R^1$ is $C_1$–$C_2$ alkyl optionally substituted by 1 to 3 fluoro substituents.

13. The process of claim 12 wherein R is cyclohexyl and $R^1$ is ethyl.

14. The process of claim 11 wherein R is cyclohexyl, $R^1$ is ethyl, and said compound of formula V is treated with the hydrochloride salt of said compound of formula VI.

15. The process of claim 10 wherein the compound of formula V is prepared by treating a compound of the formula

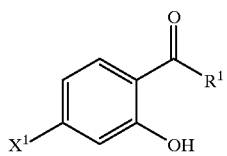

VII wherein $X^1$ and $R^1$ are as defined in claim 10, with a base and a second reagent selected from methanesulfonyl chloride, methanesulfonyl anhydride, trifluoromethanesulfonic anhydride, phenylsulfonyl chloride, and phenylsulfonyl anhydride, wherein the phenyl moieties of said phenylsulfonyl chloride and said phenylsulfonyl anhydride are optionally substituted by 1 or 2 substituents independently selected from halo, nitro and $C_1$–$C_4$ alkyl.

16. The process of claim 15 wherein said second reagent is methanesulfonyl chloride, said base is triethylamine, diisopropylethylamine, pyridine optionally substituted by 1 to 3 $C_1$–$C_6$ alkyl groups, potassium hydroxide, or sodium hydroxide, $X^1$ is bromo, and $R^1$ is $C_1$–$C_2$ alkyl optionally substituted by 1 to 3 fluoro substituents.

17. The process of claim 16 wherein said base is triethylamine, and $R^1$ is ethyl.

18. A process for preparing a compound of the formula

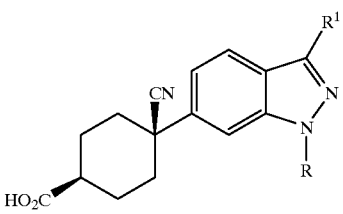

VIII or a pharmaceutically acceptable salt of said compound, wherein

R is $C_1$–$C_{10}$ alkyl or —$(CH_2)_n$(phenyl) wherein n is an integer ranging from 0 to 2, and wherein said R groups are optionally substituted by 1 to 3 substituents independently selected from chloro, fluoro, $C_1$–$C_6$ alkoxy and trifluoromethyl;

$R^1$ is $C_1$–$C_{10}$ alkyl, $C_2$–$C_6$ alkenyl or phenyl, wherein said $R^1$ groups are optionally substituted by 1 to 3 substituents independently selected from trifluoromethyl, chloro and fluoro; which comprises treating a compound of the formula

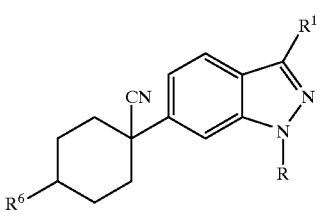

IX or a salt of said compound, wherein R and $R^1$ are as defined for said compound of formula VIII and $R^6$ is —C(O)O ($C_1$–$C_6$ alkyl), —CN, —C(O)$NR^4R^5$ or —C(O)$NR^4OR^5$ wherein $R^4$ and $R^5$ are each independently H or $C_1$–$C_6$ alkyl, with a base in an alcoholic solvent of the formula $R^7$—OH wherein $R^7$ is $C_1$–$C_6$ alkyl to provide a compound of the formula

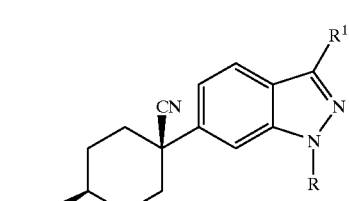

X wherein R and $R^1$ are as defined for said compound of formula IX and $R^7$ is as defined for said alcoholic solvent, and hydrolyzing the compound of formula X to provide the compound of formula VIII or a pharmaceutically acceptable salt thereof.

19. The process of claim 18 wherein said base is potassium tert-butoxide, sodium ethoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide or sodium methoxide, said alcoholic solvent is methanol, ethanol, or isopropanol, R is selected from cyclohexyl, cyclopentyl, cyclobutyl, methylene cyclopropyl and isopropyl, and $R^1$ is $C_1$–$C_2$ alkyl optionally substituted by 1 to 3 fluoro substituents.

20. The process of claim 19 wherein said base is potassium tert-butoxide, said alcoholic solvent is methanol, $R^7$ is methyl, R is cyclohexyl, and $R^1$ is ethyl.

* * * * *